(12) United States Patent
Poulard

(10) Patent No.: US 9,370,631 B2
(45) Date of Patent: Jun. 21, 2016

(54) FLUID PRODUCT DISPENSER

(71) Applicant: APTAR FRANCE SAS, Le Neubourg (FR)

(72) Inventor: Fabien Poulard, Rouen (FR)

(73) Assignee: APTAR FRANCE SAS, Le Neubourg (FR)

( * ) Notice: Subject to any disclaimer, the term of this patent is extended or adjusted under 35 U.S.C. 154(b) by 0 days.

(21) Appl. No.: 14/510,324

(22) Filed: Oct. 9, 2014

(65) Prior Publication Data

US 2015/0021357 A1 Jan. 22, 2015

Related U.S. Application Data

(63) Continuation of application No. 10/556,432, filed as application No. PCT/FR2004/011189 on May 14, 2004, now Pat. No. 8,936,177.

(30) Foreign Application Priority Data

May 15, 2003 (FR) ...................... 03 05858

(51) Int. Cl.
  *B67D 7/22* (2010.01)
  *A61M 15/00* (2006.01)
  *G06M 1/08* (2006.01)
  *G06M 3/12* (2006.01)
  *G06M 1/22* (2006.01)

(52) U.S. Cl.
  CPC .......... *A61M 15/0071* (2014.02); *A61M 15/009* (2013.01); *A61M 15/0065* (2013.01); *A61M 15/0068* (2014.02); *G06M 1/083* (2013.01); *G06M 1/22* (2013.01); *G06M 3/12* (2013.01)

(58) Field of Classification Search
  CPC .......... G06M 1/083; G06M 1/22; G06M 3/12; A61M 15/0068; A61M 15/0065; A61M 15/0071; A61M 15/009
  USPC ............ 222/36, 38, 162; 128/200.14, 200.23, 128/205.23
  See application file for complete search history.

(56) References Cited

U.S. PATENT DOCUMENTS

| | | | |
|---|---|---|---|
| 4,565,302 | A | 1/1986 | Pfeiffer et al. |
| 4,817,822 | A | 4/1989 | Rand et al. |
| 5,349,945 | A | 9/1994 | Wass et al. |
| 5,611,444 | A | 3/1997 | Garby et al. |
| 5,718,355 | A | 2/1998 | Garby et al. |
| 5,904,139 | A | 5/1999 | Hauser |
| 5,988,496 | A | 11/1999 | Bruna |
| 6,142,339 | A | 11/2000 | Blacker et al. |
| 6,155,251 | A | 12/2000 | Hauser |
| 6,161,724 | A | 12/2000 | Blacker et al. |

(Continued)

FOREIGN PATENT DOCUMENTS

| | | |
|---|---|---|
| DE | 100 61 723 A1 | 7/2002 |
| EP | 0 254 391 A1 | 1/1988 |

(Continued)

*Primary Examiner* — Lien Ngo
(74) *Attorney, Agent, or Firm* — Sughrue Mion, PLLC

(57) ABSTRACT

A fluid dispenser comprising a body (1), a fluid reservoir (2), a dispenser member, such as a pump or a valve, mounted on said reservoir (2), and a dose indicator device for indicating the number of doses of fluid that have been dispensed or that remain to be dispensed from said reservoir, the dispenser being characterized in that said dose indicator device includes a first safety system for actuating the dose indicator device once the dispenser has performed a predetermined incomplete actuation stroke, even if the dispenser does not perform the complete actuation stroke.

4 Claims, 13 Drawing Sheets

(56) References Cited

U.S. PATENT DOCUMENTS

| | | | |
|---|---|---|---|
| 6,164,494 | A | 12/2000 | Marelli |
| 6,234,148 | B1 | 5/2001 | Hartke et al. |
| 6,234,168 | B1 | 5/2001 | Bruna |
| 6,283,365 | B1 * | 9/2001 | Bason .......... 235/116 |
| 6,328,037 | B1 | 12/2001 | Scarrott et al. |
| 6,446,627 | B1 | 9/2002 | Bowman et al. |
| 6,481,438 | B1 | 11/2002 | Gallem et al. |
| 6,679,251 | B1 | 1/2004 | Gallem et al. |
| 6,752,153 | B1 | 6/2004 | Eckert |
| 7,191,918 | B2 | 3/2007 | Ouyang et al. |
| 7,232,043 | B2 * | 6/2007 | Wong et al. .......... 222/38 |
| 7,500,444 | B2 * | 3/2009 | Bonney .......... A61M 15/0065 116/311 |
| 7,650,883 | B2 | 1/2010 | Scarrott et al. |
| 2002/0195102 | A1 | 12/2002 | Rand et al. |

FOREIGN PATENT DOCUMENTS

| | | |
|---|---|---|
| EP | 0 480 488 A1 | 4/1992 |
| EP | 0 949 584 A2 | 10/1999 |
| EP | 1 010 438 A1 | 6/2000 |
| EP | 1 065 477 A2 | 1/2001 |
| EP | 1 163 922 A2 | 12/2001 |
| WO | 93/24167 A1 | 12/1993 |
| WO | 98/52634 A1 | 11/1998 |
| WO | 98/56444 A1 | 12/1998 |
| WO | 00/09187 A1 | 2/2000 |
| WO | 00/21593 A1 | 4/2000 |
| WO | 00/59806 A1 | 10/2000 |
| WO | 01/28887 A1 | 4/2001 |
| WO | 01/37909 A1 | 5/2001 |

* cited by examiner

FLUID PRODUCT DISPENSER

CROSS REFERENCE TO RELATED APPLICATIONS

This is a continuation application of U.S. patent application Ser. No. 10/556,432, filed Nov. 9, 2005, which is the National Stage of International Application No. PCT/FR2004/001189 filed May 14, 2004, claiming priority based on French Patent Application No. 03/05858, filed May 15, 2003, the disclosures of which are hereby incorporated by reference.

TECHNICAL FIELD

The present invention relates to a fluid dispenser, and more particularly to such a dispenser including a dose indicator device for indicating to the user the number of doses that have been dispensed or that remain to be dispensed from the reservoir of said fluid dispenser.

BACKGROUND

Dose indicator devices are well known, and can include either counters, displaying a number corresponding to the number of doses that have been dispensed or that remain to be dispensed, or indicators, informing the user by means of symbols, color codes, or similar numbers, about the number of doses that have been dispensed or that remain to be dispensed. In particular, in fluid dispensers containing pharmaceuticals, it is important for the dose indicator device to function in reliable manner, and in particular for it to count the dispensing of a dose each time the fluid is dispensed, regardless of whether the dose is complete or incomplete, e.g. because of accidental actuation or actuation that is interrupted before the end of the actuation cycle. It is generally preferable for the dispensing of an incomplete dose to be counted as a complete dose rather than for it not to be counted at all, since failure to count could present a high risk to the user, informing the user of a reservoir content that is greater than the reality. In dispensers of pharmaceuticals, it is thus generally desirable to avoid any risk of under-counting, in particular by triggering counting just before the active substance is expelled. Another important point with dose indicator devices for dispensers of pharmaceuticals is that once actuation has taken place and a dose has been dispensed, while the dispenser is returning to its rest position, any further actuation that is performed before the end of the return stroke of the dispenser, and that would cause a complete or incomplete dose to be dispensed, should also be counted by the indicator device, likewise to avoid any risk of under-counting. In most fluid dispensers, once a dose has been dispensed, the next dose is loaded into the chamber of the dispenser member (pump or valve) while the dispenser is returning to its rest position. In order to avoid any risk of under-counting during the return stroke of the dispenser, it is desirable for the fluid dispenser to be blocked as soon as the return stroke has allowed the chamber to be filled, and until the indicator device is once again able to count the actuation of the dispenser.

SUMMARY

An object of the present invention is to provide a fluid dispenser which satisfies one or more of the above-mentioned requirements.

In particular, an object of the present invention is to provide a fluid dispenser including a dose indicator device that prevents any risk of under-counting, i.e. that guarantees that the indicator device is actuated each time fluid is dispended by the fluid dispenser.

When the actuation of the dispenser does not cause any fluid to be dispensed, another object of the present invention is to provide such a dispenser that prevents dose dispensing from being counted, and thus prevents the dose indicator device from being actuated.

Another object of the present invention is to provide such a fluid dispenser that is simple and inexpensive to manufacture and to assemble, and that is reliable in use.

The present invention thus provides a fluid dispenser comprising a body, a fluid reservoir, a dispenser member, such as a pump or a valve, mounted on said reservoir, and a dose indicator device for indicating the number of doses of fluid that have been dispensed or that remain to be dispensed from said reservoir, the dispenser being characterized in that said dose indicator device includes a first safety system for actuating the dose indicator device once the dispenser has performed a predetermined incomplete actuation stroke, even if the dispenser does not perform the complete actuation stroke.

Preferably, said dose indicator device includes a second safety system which, during the return stroke of the dispenser after dispensing a dose, prevents the pharmaceutical from being expelled again until said dispenser has completed a predetermined incomplete return stroke, said dispenser and said dose indicator device being capable of being actuated once again, once the predetermined incomplete return stroke has been performed, even if the dispenser does not perform the complete return stroke and said dispenser is actuated once again before returning to it rest position.

Advantageously, said reservoir is axially displaceable relative to said body, said body including at least one stationary gear, said dose indicator device including a counter element that is displaceable axially and in rotation relative to said body, said counter element co-operating, while the dispenser is being actuated, firstly with said at least one stationary gear of said body, and secondly with said reservoir.

In a first embodiment of the invention, said body includes a stationary gear co-operating with a first gear of said counter element, said counter element including a second gear co-operating with an actuator gear of an actuator member of the dispenser, the teeth of said second gear and/or of said actuator gear being made so that axial displacement of the actuator member causes said counter element to be displaced axially and in rotation, the stationary gear preventing said counter element from turning until said counter element no longer co-operates with said stationary gear, after a predetermined axial displacement of said counter element corresponding to said predetermined incomplete actuation stroke of the dispenser.

The stationary gear advantageously includes abutment means preventing said counter element from turning once said counter element has turned at least in part, an additional axial displacement of said counter element being necessary to enable it to continue to turn and/or to return the indicator device to its rest position. These abutments position the second gear of the counter element in such a manner that the dispenser is blocked on its return prior to the chamber being filled and until its rest position.

Advantageously, said abutment means comprise an axial projection.

Advantageously, said stationary gear and/or said counter element include(s) blocking means preventing the dispenser from being actuated once again, and thus preventing any pharmaceutical from being expelled once again, while the counter element is returning to its rest position after a preceding actuation, and until the dispenser has completed a predetermined incomplete return stroke, after which the indicator device can count the next dose.

Advantageously, said blocking means comprise axial projections provided on the body and on the counter element respectively, each of said projections having an axial end-profile that is plane, said projections facing each other, at least in part, until the counter element has turned sufficiently to offset said projections, with that sufficient turn corresponding to said predetermined incomplete return stroke of the dispenser.

Advantageously, the teeth of the second gear of the counter element include an intermediate step, the actuator member co-operating with said step while the dispenser is being actuated, and co-operating with the end wall of said second gear while returning to the rest position, after being actuated, the displacement between the intermediate step and the end wall being obtained by said counter element turning.

Advantageously, once the predetermined incomplete return stroke has been performed, the actuator member is positioned facing the following tooth of the second gear of the counter element, enabling the dispenser and the dose indicator device to be actuated once again.

In a second embodiment of the present invention, said body includes a first stationary gear and a second stationary gear, said counter element including a first gear for co-operating with said first stationary gear and a second gear for co-operating with said second stationary gear, said counter element being put axially into contact with the actuator member of the dispenser by means of a return spring and being turnable relative to said actuator member, the teeth of said second gear and of said second stationary gear being oblique, at least in part, so that an axial displacement of the actuator member initially causes said counter element to be displaced axially over a predetermined incomplete actuation stroke until the oblique portion of said second gear of the counter element co-operates with said oblique portion of said second stationary gear, causing the counter element to be turned over a first portion of a turn cycle, the teeth of said first gear and of said first stationary gear being oblique, at least in part, so that when the counter element returns to its rest position, it is caused to turn so as to terminate its turn cycle, which corresponds to one actuation of the dispenser being counted.

Advantageously, said first and second stationary gears of the body and/or said first and second gears of the counter element are offset relative to each other, so that whenever the counter element is displaceable in rotation, returning said counter element to its rest position without terminating the actuation stroke of the dispenser causes the counter element to turn over its complete turn cycle, guaranteeing that one actuation of the dispenser is counted after said predetermined incomplete actuation stroke.

Advantageously, said second stationary gear of the body and/or said second gear of the counter element include(s) blocking means preventing the dispenser from being actuated once again, and thus preventing any pharmaceutical from being expelled once again, while the counter element is returning to its rest position following a preceding actuation, and until said dispenser has performed a predetermined incomplete return stroke, after which the indicator device can count the next dose.

Advantageously, said blocking means have an axial end-profile that is plane, at least in part, and that is formed on the teeth of said second stationary gear of the body and on the teeth of said second gear of the counter element, said plane profiles of said teeth facing each other, at least in part, until the counter element has completed a turn that is sufficient to offset said teeth, with that sufficient turn corresponding to said predetermined incomplete return stroke of the dispenser.

Advantageously, said actuator member of the dispenser is secured to said reservoir and is displaced axially therewith.

In a third embodiment of the present invention, said body includes a first stationary gear and a second stationary gear, said counter element comprising a first gear for co-operating with said first stationary gear, a second gear for co-operating with said second stationary gear, and a third gear for co-operating with an actuator gear secured to an actuator member of the dispenser, the teeth of said third gear and/or of said actuator gear being made so that axial displacement of the actuator member causes said counter element to be displaced axially and in rotation, the first stationary gear preventing said counter element from turning until said counter element no longer co-operates with said stationary gear, after a predetermined axial displacement of said counter element corresponding to said predetermined incomplete actuation stroke of the dispenser.

Advantageously, said second stationary gear of the body and/or said second gear of the counter element include(s) blocking means preventing the dispenser from being actuated once again, and thus preventing any pharmaceutical from being expelled once again, while the counter element is returning to its rest position following a preceding actuation, until said dispenser has performed a predetermined incomplete return stroke, after which the indicator device can count the next dose.

Advantageously, said blocking means have an axial end-profile that is plane and that is formed on the teeth of said second stationary gear and on the teeth of said second gear, said teeth facing each other, at least in part, until the counter element has completed a turn that is sufficient to offset said teeth, with that sufficient turn corresponding to said predetermined incomplete return stroke of the dispenser.

Advantageously, said actuator gear includes abutment means limiting the extent to which the counter element can turn, until the actuator member has performed said predetermined incomplete return stroke.

Advantageously, said abutment means comprise an axial projection formed on said actuator gear.

Advantageously, said actuator member of the dispenser is secured to said reservoir and is displaced axially therewith.

BRIEF DESCRIPTION OF THE DRAWINGS

Other characteristics and advantages of the present invention appear more clearly from the following detailed description of three embodiments thereof, given by way of non-limiting example, and with reference to the accompanying drawings, and in which.

DETAILED DESCRIPTION

Figure 1:
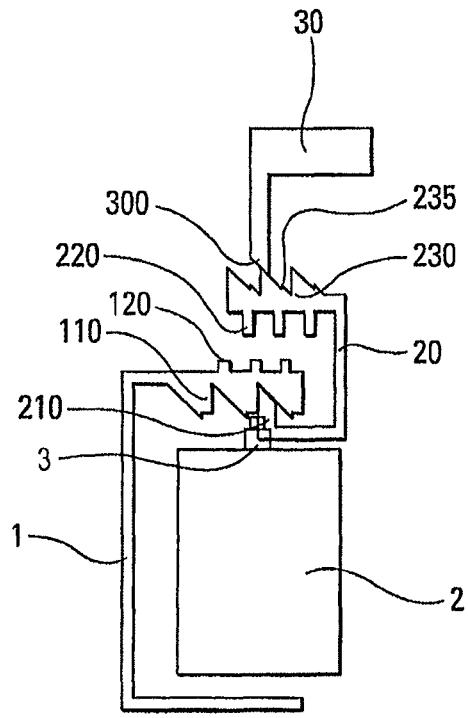
FIGS. 1 to 8 are diagrams of a fluid dispenser constituting a first embodiment of the present invention, showing the successive positions of the dispenser during an actuation cycle.
Figure 2:
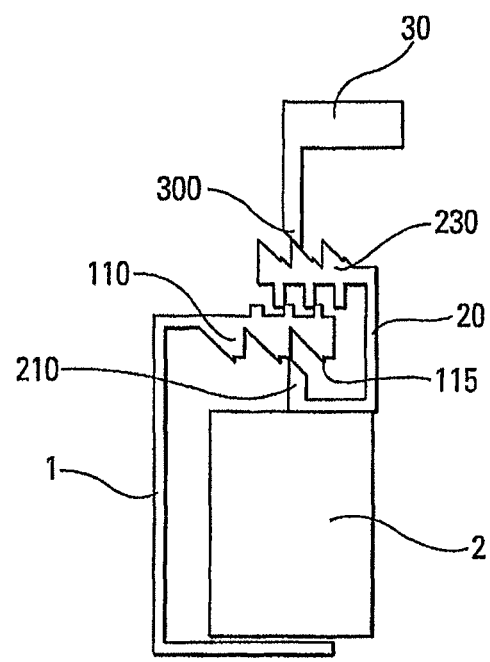

The descriptions of the three embodiments below relate to actuation cycles of the dispenser, and to the various functional features of the indicator device that make it possible to guarantee operational and counting reliability of said indicator device. The drawings to which the present description refers are therefore highly simplified diagrams which do not show the fluid dispenser in detail, but only in very diagrammatic manner relating to the various portions that can be moved relative to one another, for explaining the actuation cycle of said dispenser and of said indicator device.

It should be observed that the present invention applies more particularly to "Metered Dose Inhaler" (MDI) devices which comprise a metering valve mounted on a reservoir containing the fluid and a propellant gas, the displacement of the reservoir relative to the valve member causing a dose of fluid to be dispensed by means of said propellant gas. The present invention is not limited to that particular application, but said application represents the preferred application of the present invention.

With reference to FIGS. 1 to 8, a first embodiment of the present invention is described. The dispenser includes the body 1, the reservoir 2, and a dispenser member 3 mounted on a reservoir 2. In this first embodiment, the dispenser includes a reservoir 2 that is axially displaceable in a body 1, which is considered below as being the stationary portion of the dispenser. The axial displacement of the reservoir 2 relative to the body 1 actuates the dispenser member 3 (shown in FIG. 1) and thus causes a dose of fluid to be dispensed from said reservoir. In this first embodiment, the dispenser includes an actuator member 30 on which the user exerts an axial actuation force so as to actuate the dispenser and thus displace said reservoir 2 relative to the body 1. The dispenser further includes a dose indicator device for counting or indicating the dispensing of one fluid dose each time the dispenser is actuated. Thus, by means of the indicator device, the user can tell how many doses have been dispensed from said reservoir 2, or how many doses remain inside said reservoir 2. This information must be very accurate, in particular when the fluid is a pharmaceutical, and any risk of under-counting must be eliminated. In the event of under-counting, i.e. in the event of the indicator device failing to count one or more occasions on which a dose of fluid is dispensed in full or in part, the user can end up with a dispenser that indicates that one or two doses remain in the reservoir, whereas in reality, the reservoir is empty. In the event of an asthma attack, the user can thus end up with a dispenser that is no longer functional, and that does not enable the user to take the medicine.

The present invention makes it possible to avoid any risk of under-counting. To do this, the dose indicator device includes at least one safety system, and preferably two. The first safety system guarantees that the dose indicator device is actuated, and thus that the dispensing of a dose of fluid is counted, as soon as the dispenser, on being actuated, has traveled along a predetermined incomplete stroke. The second safety system is for preventing a dose from being expelled during the return stroke of the dispenser, while the dose indicator device is not ready to count the next dose. The dosage chamber of the dispenser is generally filled while the dispenser is returning to its rest position, after a preceding actuation. If the return stroke is not complete, but the device is actuated once again before it has returned to its rest position, it is possible for some fluid to be dispensed. However, if the dose indicator device has not returned to, or close to, its rest position, this dispensing of fluid cannot be counted. Under-counting would thus occur. In order to avoid this, the second safety system blocks any new actuation, or at least any new dispensing of fluid. Blocking is performed until the return stroke is sufficient for the dose indicator device to be actuated once again, and for it to be able to count the next dose.

In short, the present invention provides one or two safety systems that avoid any risk of the indicator device under-counting.

Initially, the first safety system is described below with reference to FIGS. 1 to 4.

With reference to these figures, it should be observed that the stationary body 1 includes a stationary gear 110, and that the indicator device comprises a counter element 20 for co-operating firstly with said stationary gear 110 of the body 1, and secondly with the actuator member 30 and/or the reservoir 2. More particularly, the counter element 20 is displaceable both axially and in rotation relative to the body 1. The counter element 20 includes a first gear 210 for co-operating with said stationary gear 110 of the body, and a second gear 230 for co-operating with an actuator gear 300 secured to the actuator member 30.

Figure 3:
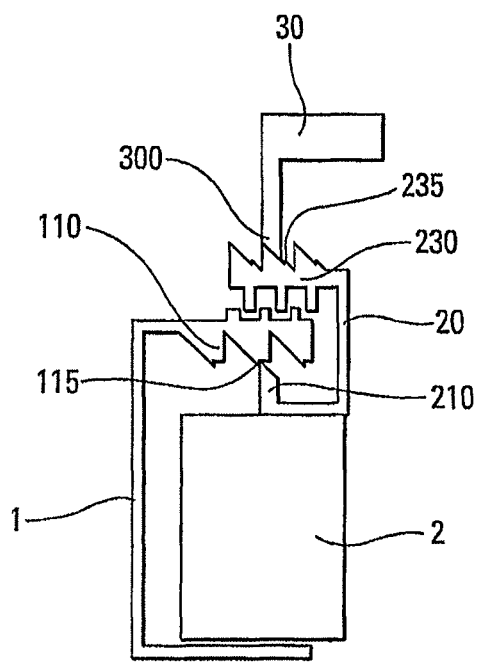
Figure 4:
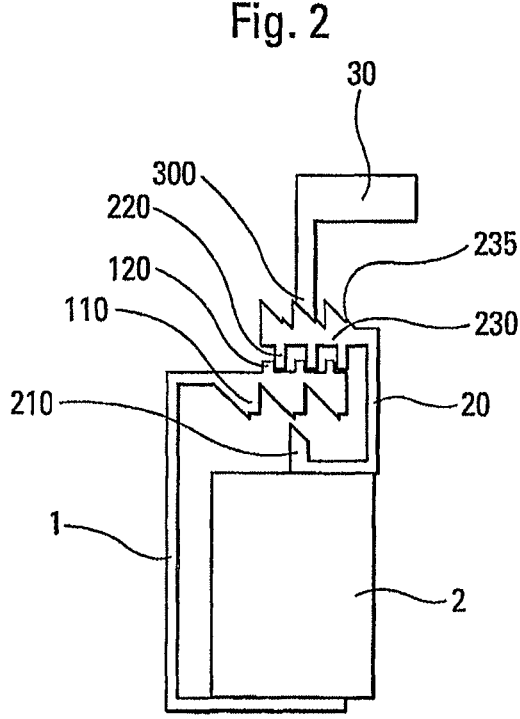

FIGS. 1 to 4 show the first half of an actuation cycle of the dispenser, i.e. the displacement of the dispenser from the rest position (shown in FIG. 1) to the actuated position (shown in FIG. 4). Thus, when the user presses on the actuator member 30 so as to displace said actuator member axially downwards in FIG. 1, the oblique profile of the teeth of the actuator gear 300 and of the second gear 230 of the counter element urge the counter element 20 to be displaced axially downwards, and also in rotation because of the oblique profile of the above-mentioned gears. However, while the first gear 210 of the counter element 20 is co-operating with the stationary gear 110 of the body 1, the counter element 20 is prevented from turning at all. Consequently, at the start of the actuation stroke of the dispenser, and thus of the actuator member 30, the counter element 20 can be displaced only axially together with the actuator member 30, without being able to turn. When the system reaches the position shown in FIG. 2, the axial displacement of the counter element 20 has also caused the reservoir 2 to be displaced axially over a first fraction of the actuation stroke. In the position shown in FIG. 2, the first gear 210 of the counter element 20 reaches a position in which it no longer co-operates with the stationary gear 110 of the body 1. As a result, the counter element, which is urged to turn by the force exerted on the actuator member 30, can turn relative to the body 1. As soon as the counter element starts to turn a little, the dose indicator device is actuated and the counting of one dose of fluid is initiated. This incomplete axial displacement stroke of the counter element 20 corresponds to said predetermined incomplete actuation stroke of the dispenser, and more particularly of the reservoir 2. In this type of dispenser, the dose of fluid is not necessarily expelled at the end of the actuation stroke, but starting from a predetermined incomplete stroke, which is itself a function of the displacement of the valve member, or a function of the displacement of the piston in a pump. By making the co-operation of the first gear 210 of the counter element with the stationary gear 110 of the body 1 correspond with said predetermined incomplete actuation stroke of the dispenser, it is ensured that, as soon as there is any possibility of the fluid being dispensed from the reservoir 2, then the indicator device counts one dose as being dispensed.

FIG. 3 shows that the stationary gear 110 of the body 1 includes abutment means 115, preferably formed by an axial projection co-operating with the first gear 210 of the counter element 20, and which abutment means cause the counter element to be axially displaced once again, by a very small but non-zero amount, so as to enable sufficient meshing of the actuator gear 300 in the first step, defined by the abutment 235 on the second gear 230. Thus, the chamber of the dispenser cannot be filled unless the abutment 235 has been passed over. Once it has been passed over, the actuator gear 300 is positioned at the second step or the end wall of the second gear 230 of the counter element 20, before the dispenser chamber is filled, so as to prevent the pharmaceutical from being expelled, as shown in FIG. 6.

Continuing the actuation stroke brings the reservoir 2 into the position shown in FIG. 4, in which the complete actuation stroke has been performed, and the entire dose has been expelled from the reservoir. However, it should be observed that even if the user ceases to exert force on the actuator member 30 before the end of the complete actuation stroke, the indicator device counts the dispensing of one dose as soon as the incomplete actuation stroke has been performed, so that any under-counting is prevented thereby.

Figure 5:
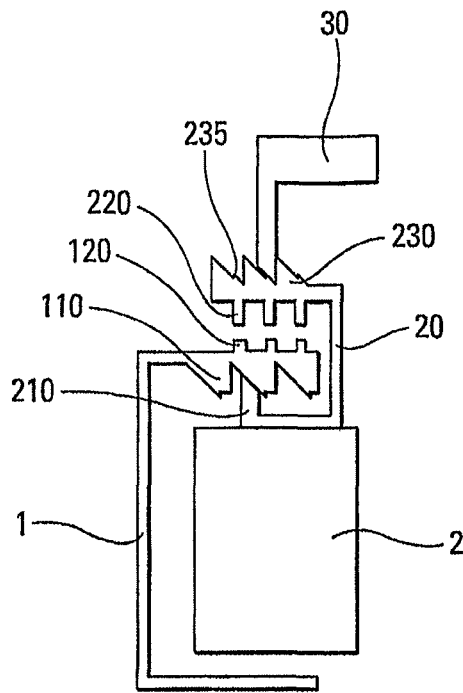
Figure 6:
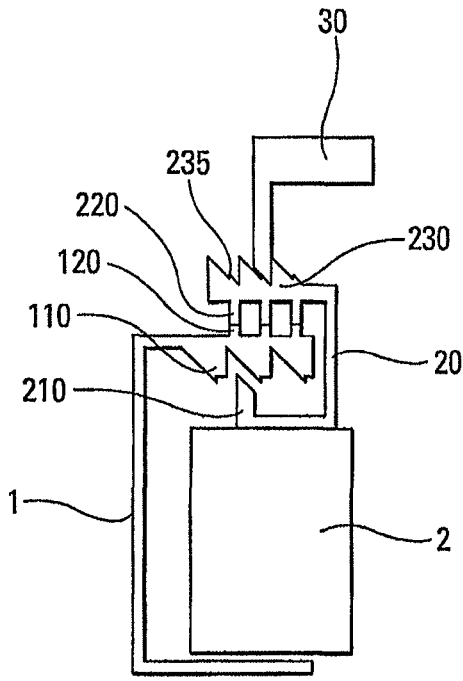
Figure 7:
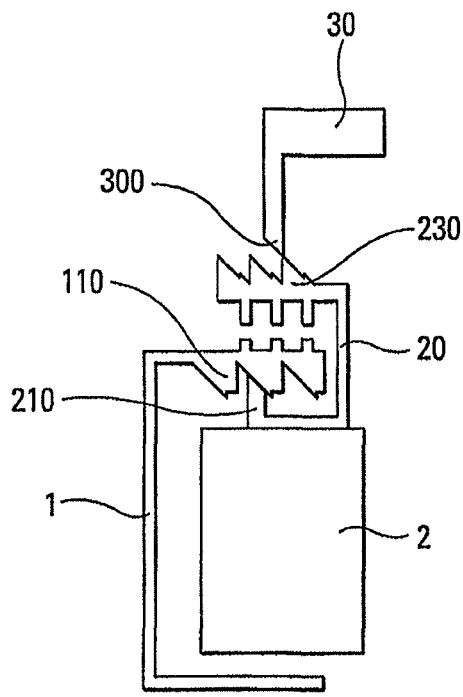
Figure 8:
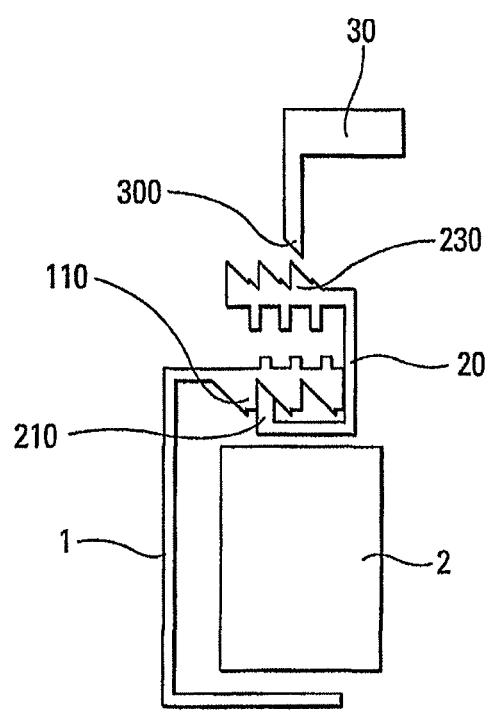

With reference to FIGS. 5 to 8, the second stage of the actuation cycle of the dispenser is described below, namely the return from the dispensing position to the rest position (shown in FIG. 8). With reference to FIG. 5, it should be observed that when the user releases the pressure on the actuator member 30, the return spring (not shown) of the dispenser returns the reservoir 2 to its rest position by displacing the reservoir 2 axially relative to the body 1 in the direction opposite to the direction of the above-described actuation displacement. The displacement of the reservoir 2 causes the counter element 20 to be axially displaced, so that the first gear 210 comes to co-operate once again with the stationary gear 110 of the body 1, but this time via the oblique portions, thereby causing said counter element to turn, so as to terminate the counting cycle of the indicator device. While the counter element is turning relative to the body 1 during the return stroke, it should be observed that the actuator member 30 comes to co-operate with the end wall of the second gear 230 of the counter element 20, whereas during the actuation stage, the actuator gear 300 co-operates with the first step, defined by the abutment 235, formed on said second gear 230 of the counter element 20.

FIG. 6 is a diagram showing an attempt to perform a new actuation before the dispenser has completed its return stroke. It should be observed that the body 1 includes axial projections 120 that co-operate with axial projections 220 formed on the counter element 20. In a variant, the axial projections 120, 220 can be replaced by gears 122, 222 of corresponding shape. Preferably, the axial end-profiles of said projections 120 and 220 are formed by planes, and the axial projections 120 and 220 are disposed facing each other, at least in part, so that if the return stroke of the dispenser is insufficient, it is impossible to expel a new dose of fluid, as shown in FIG. 6. In order to be able to actuate the dispenser once again, it is necessary for the counter element 20 to turn sufficiently about its axis of rotation, for said projections 120 and 220 to be offset relative to each other, thereby enabling a new actuation. The offset is achieved by freeing the actuator member 30 from the end wall of the second gear 230 of the counter element 20, so as to position it facing the first step, defined by the abutment 235 of the following tooth. The new actuation can be permitted before the dispenser has completed its return stroke, as soon as the indicator device is once again capable of counting a new actuation of the dispenser. The present invention makes it possible to fulfill this requirement, as shown in FIG. 7, in which the return stroke is not complete, but the actuator member 30 of the dispenser, and in particular the actuator gear 300, is in a position in which it can co-operate with the next tooth of the second gear 230 of the counter element, so that a new actuation at this moment causes the counter element to turn through the end of its preceding cycle, thereby causing said axial projections 120 and 220 to be offset, and thus enabling the dispenser and the dose indicator device to be actuated once again. The aim is to prevent expulsion when the chamber is full, so long as the counter is not ready to count another dose.

In FIG. 8, the device is returned to its initial rest position and a new actuation cycle can be performed.

Figure 9:
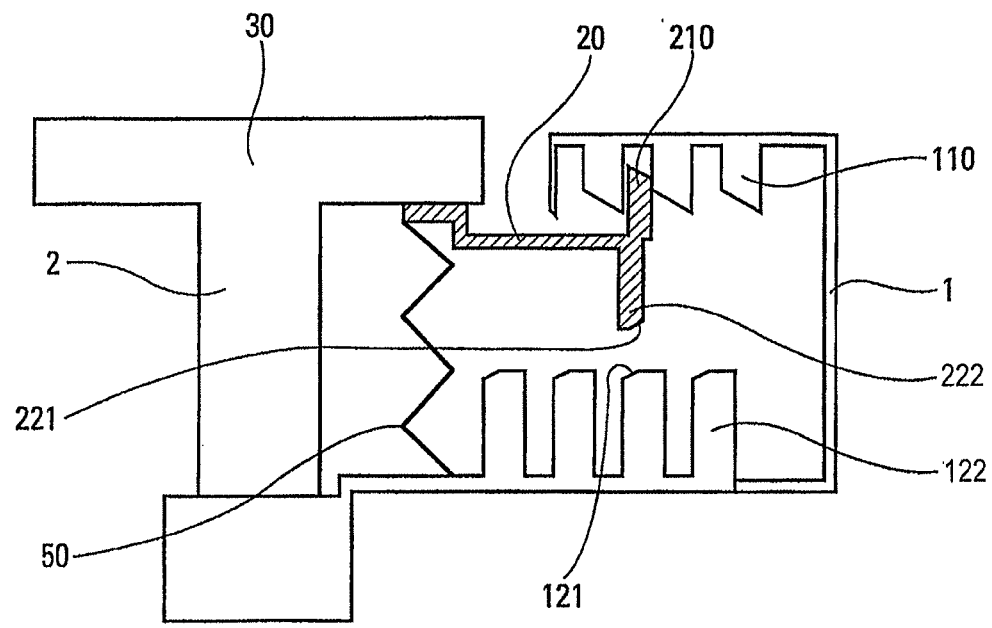
FIGS. 9 to 12 are diagrams of a dispenser constituting a second embodiment of the present invention, also showing various positions of the dispenser during the actuation cycle.
Figure 10:
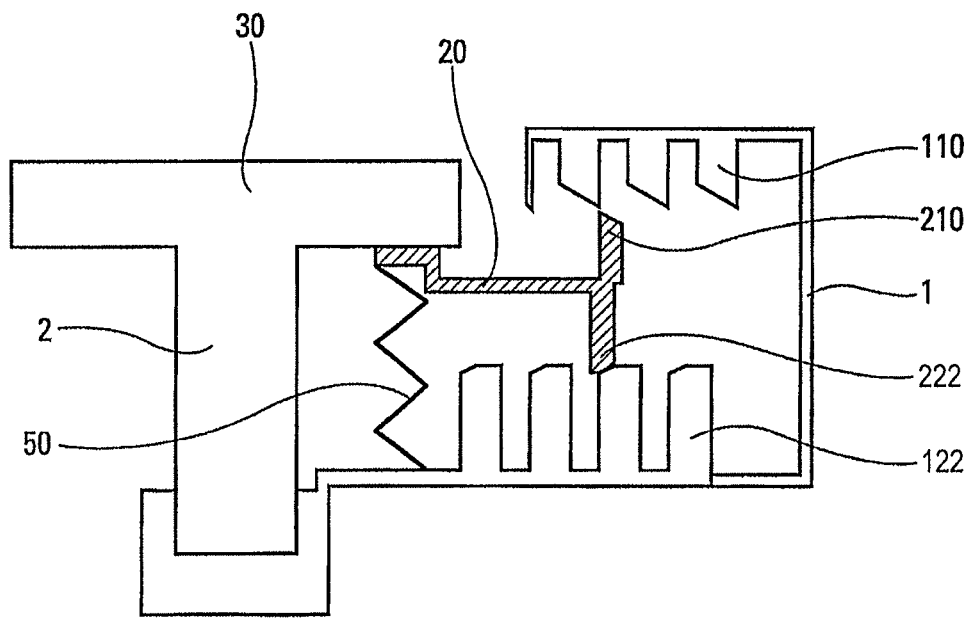

FIGS. 9 to 12 show a second embodiment of the invention. The second embodiment differs from the first embodiment as follows: Firstly, the body 1 includes two stationary gears 110 and 122, and the counter element 20 includes two gears 210, 222, each co-operating with one of the stationary gears of the body. The stationary gear 122 and the gear 222 are used in this embodiment in place of the axial projections 120 and 220. The actuator member 30 is secured to the reservoir 2, and the counter element 20 is axially displaceable with said actuator member 30. It can be turned relative to said actuator member 30. In fact, in the second embodiment, there is not really an actuator member, but the user generally displaces the reservoir 2 itself, relative to the body 1, so as to perform the actuation. The second stationary gear 122 of the body 1 and the second gear 222 of the counter element include respective portions 121 and 221 that are oblique, at least in part, and said portions co-operate with each other while the dispenser is being actuated. The oblique portions urge the counter element 20 to turn, and thus initiate a counting cycle of the dose indicator device. As shown in FIGS. 9 and 10, while the dispenser is being actuated, the counter element is firstly displaced axially without turning, by being secured to the actuator member 30 and the reservoir 2. Once the dispenser has performed the predetermined incomplete actuation stroke, the oblique portions 121, 221 of the second gears 122, 222 co-operate so as to cause the actuator member to turn, as shown in FIG. 10.

It should be observed that if, in the position shown in FIG. 10, the user stops actuating the dispenser, the system returns to its rest position by means of a return spring 50, and the counting cycle is completed since the first gear 210 of the counter element 20 comes to co-operate with the teeth of the first stationary gear 110 so as to urge the counter element 20 to turn even more, in order to bring it to the end of its counting cycle. The first safety system is thus provided in that the actuation of the dose indicator device is ensured as soon as the dispenser has performed its predetermined incomplete actuation stroke, from which at least some fluid can be dispensed (a full dose or an incomplete dose).

Figure 11:
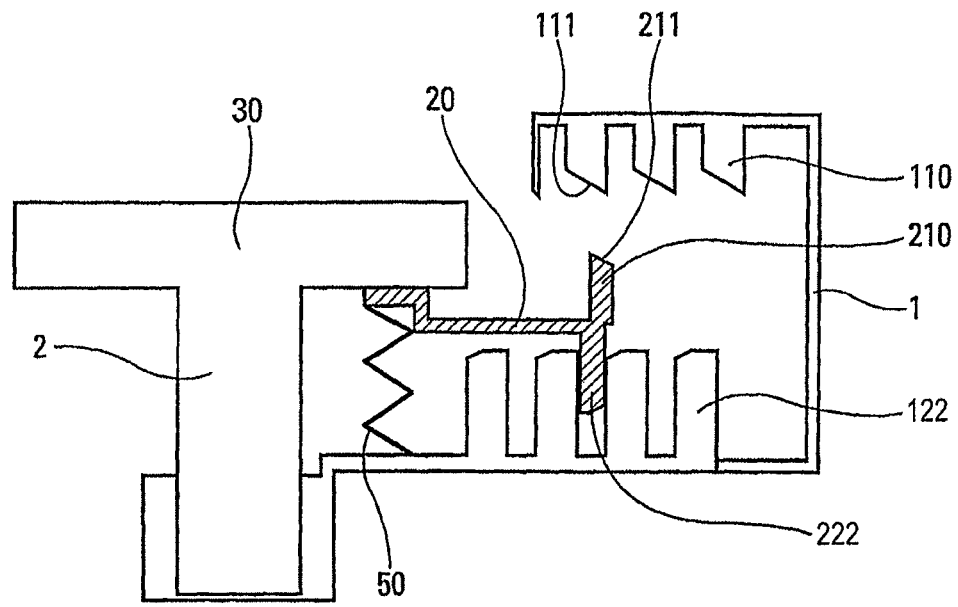
Figure 12:
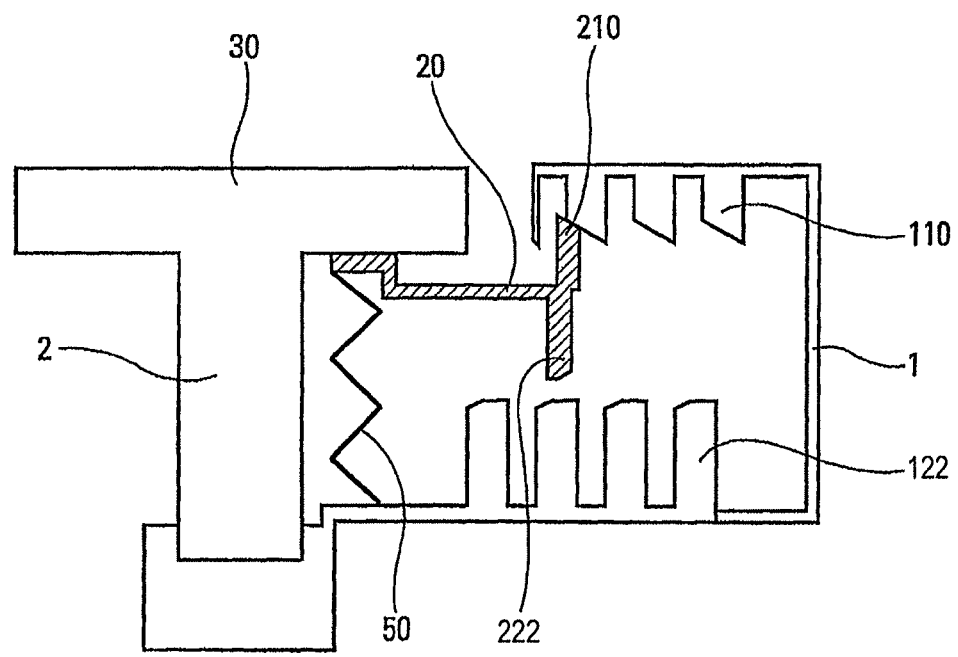
Figure 13:
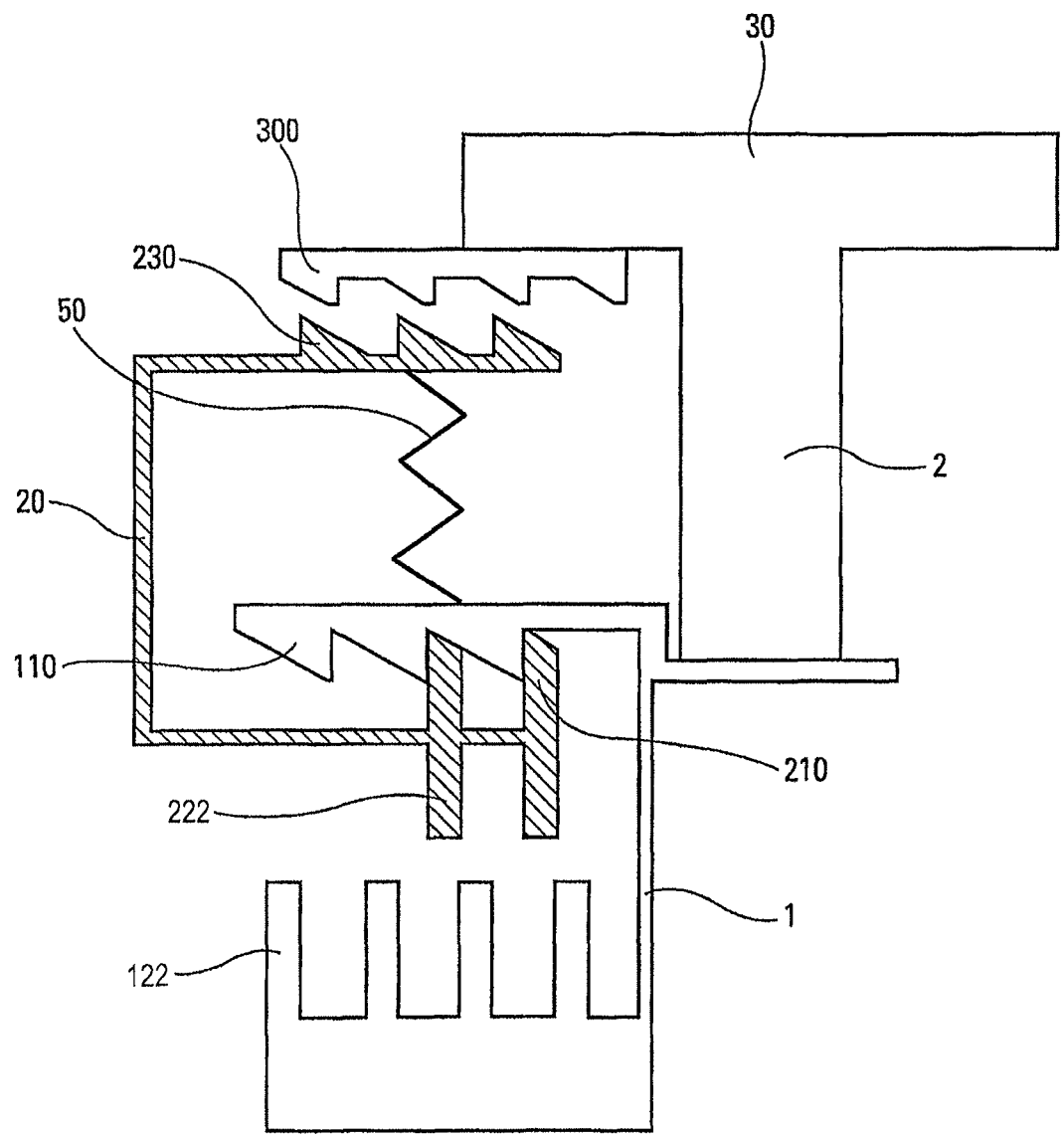
FIGS. 13 to 21 are diagrams of a fluid dispenser constituting a third embodiment of the present invention, showing various positions of the dispenser during the actuation cycle.
Figure 14:
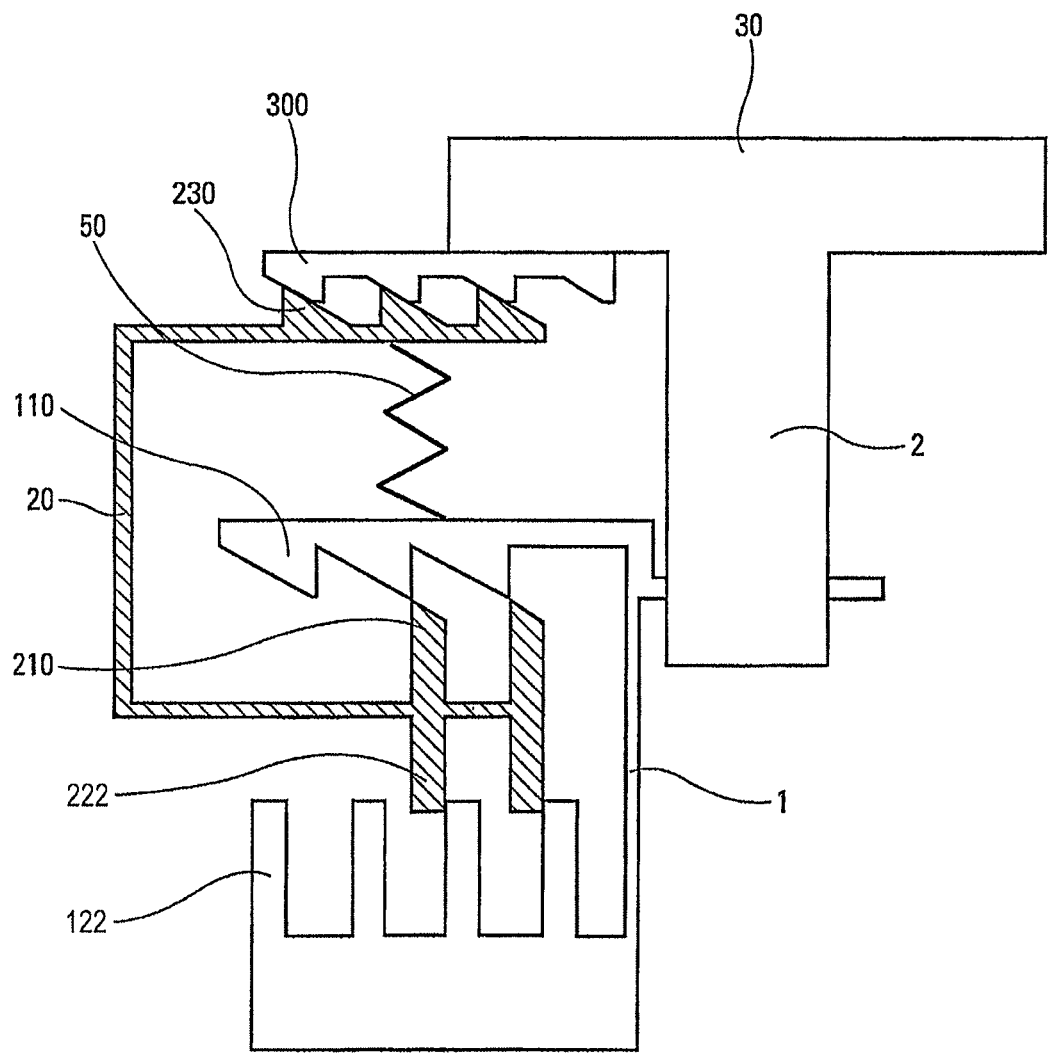

FIG. 11 shows the actuated position in which the complete actuation stroke has been performed, and FIG. 12 shows the second safety means, provided by means of the second stationary gear 122, and the second gear 222 of the counter element 20. The two gears also include respective plane portions, each having a plane axial end-profile, so that when the return stroke of the dispenser is not sufficient, as can be seen in FIG. 12, a new actuation of the system brings the counter element 20 into axial abutment with the second stationary gear 122 via their plane end-portions, thereby preventing any pharmaceutical from being expelled, by preventing the dispenser from being actuated. It is only once a predetermined incomplete return stroke has been performed that the oblique portions of the second gears 122 and 222 are facing each other, so as to enable the dispenser and the dose indicator device to be actuated once again.

Figure 15:
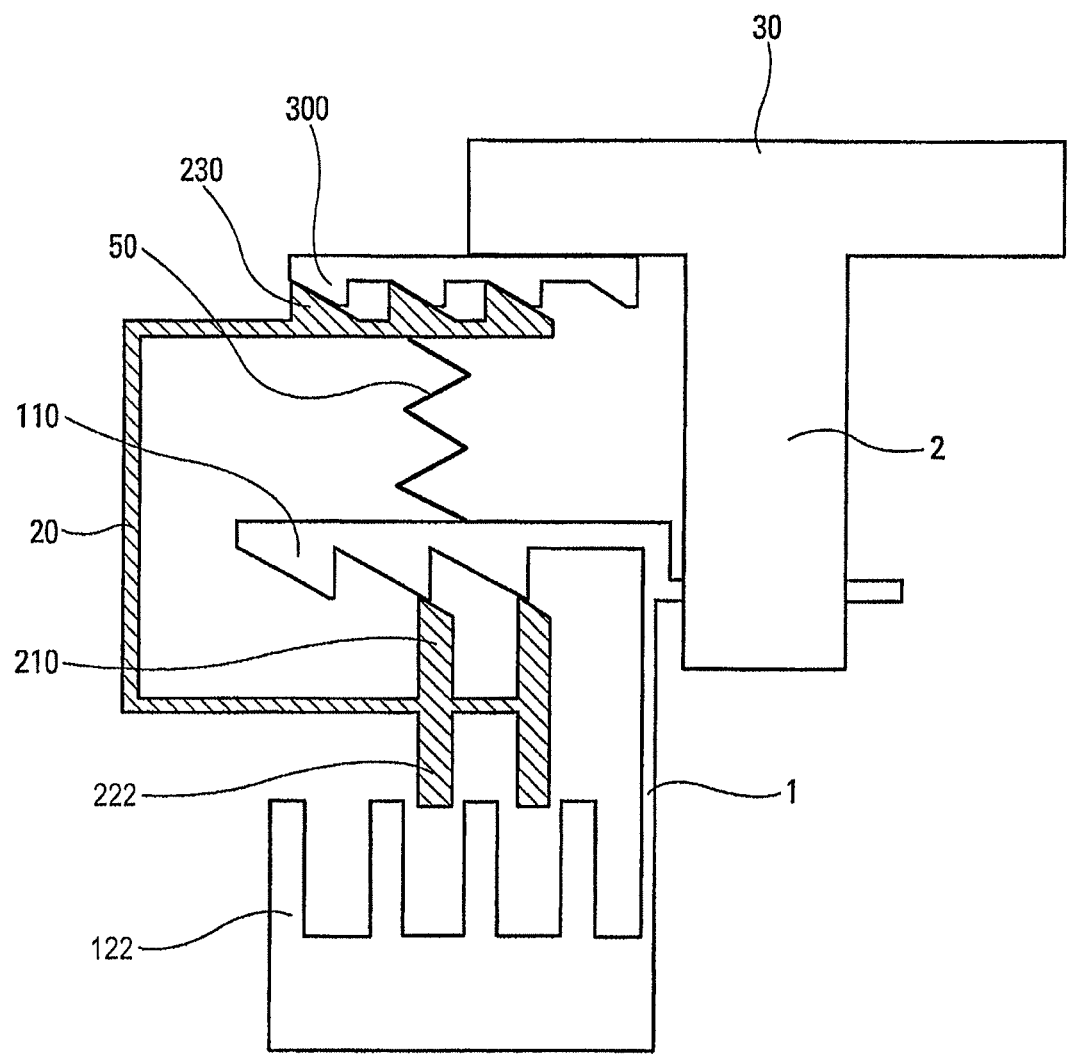

FIGS. 13 to 21 show a third embodiment of the present invention. The third embodiment differs from the second embodiment in that the counter element 20 is not axially secured to the actuator member 30 and to the reservoir. The actuator member 30 and the reservoir 2 include an actuator gear 300 that co-operates with a third gear 230 provided on the counter element 20. In the third embodiment, turning of the counter element 2.0 during the actuation stroke of the dispenser is thus no longer caused by the second stationary gear 122, but by means of the third gear 230 and the actuator gear 300. The third embodiment is thus a combination of the first and second embodiments described above. At the start of actuation, when in the situation in FIG. 13, the co-operation between the first stationary gear 110 and the first gear 210 of the counter element 20, prevents the counter element 20 from turning, and thus causes said counter element to be axially displaced. When in the position shown in FIG. 14, the above-mentioned first gears no longer co-operate, and the oblique profiles of the teeth of the actuator gear 300 and of the third gear 230 of the counter element 20, cause the counter element 20 to turn. This takes place after said incomplete actuation stroke of the dispenser, after which a complete or incomplete dose of fluid can be dispensed. FIG. 15 shows that if the axial actuation force is eliminated at this moment, the return spring 50 causes the counter element to turn through its complete counting cycle, thereby preventing any risk of under-counting.

Figure 16:
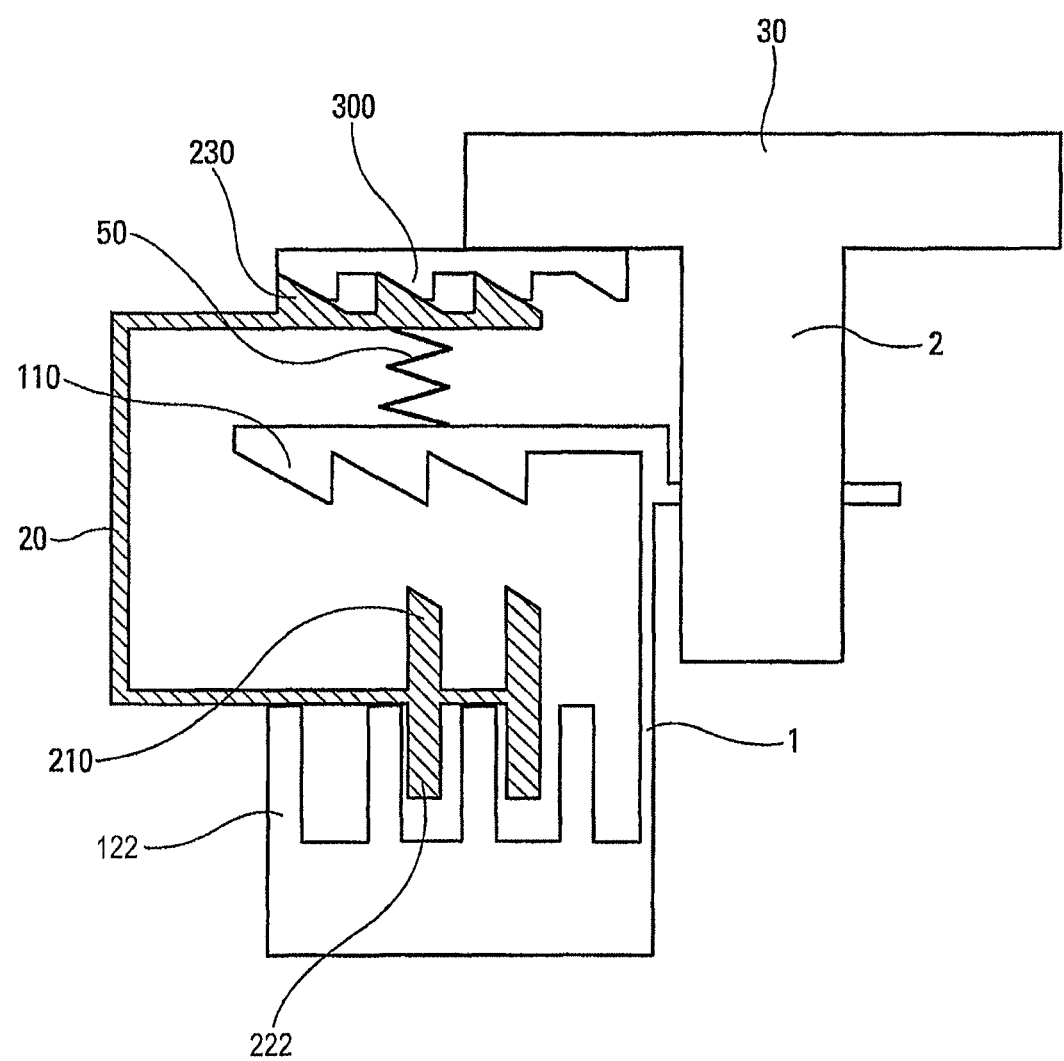
Figure 17:
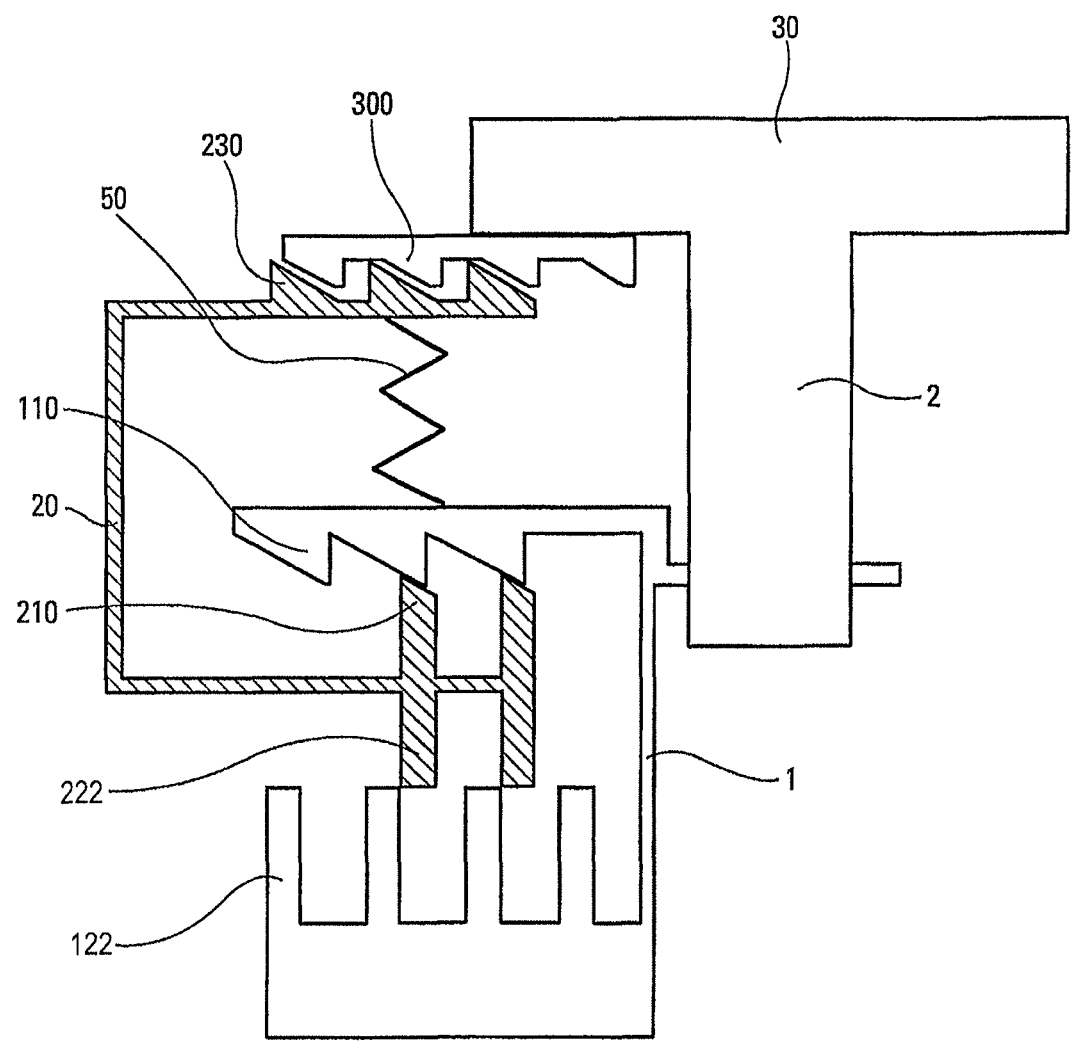
Figure 18:
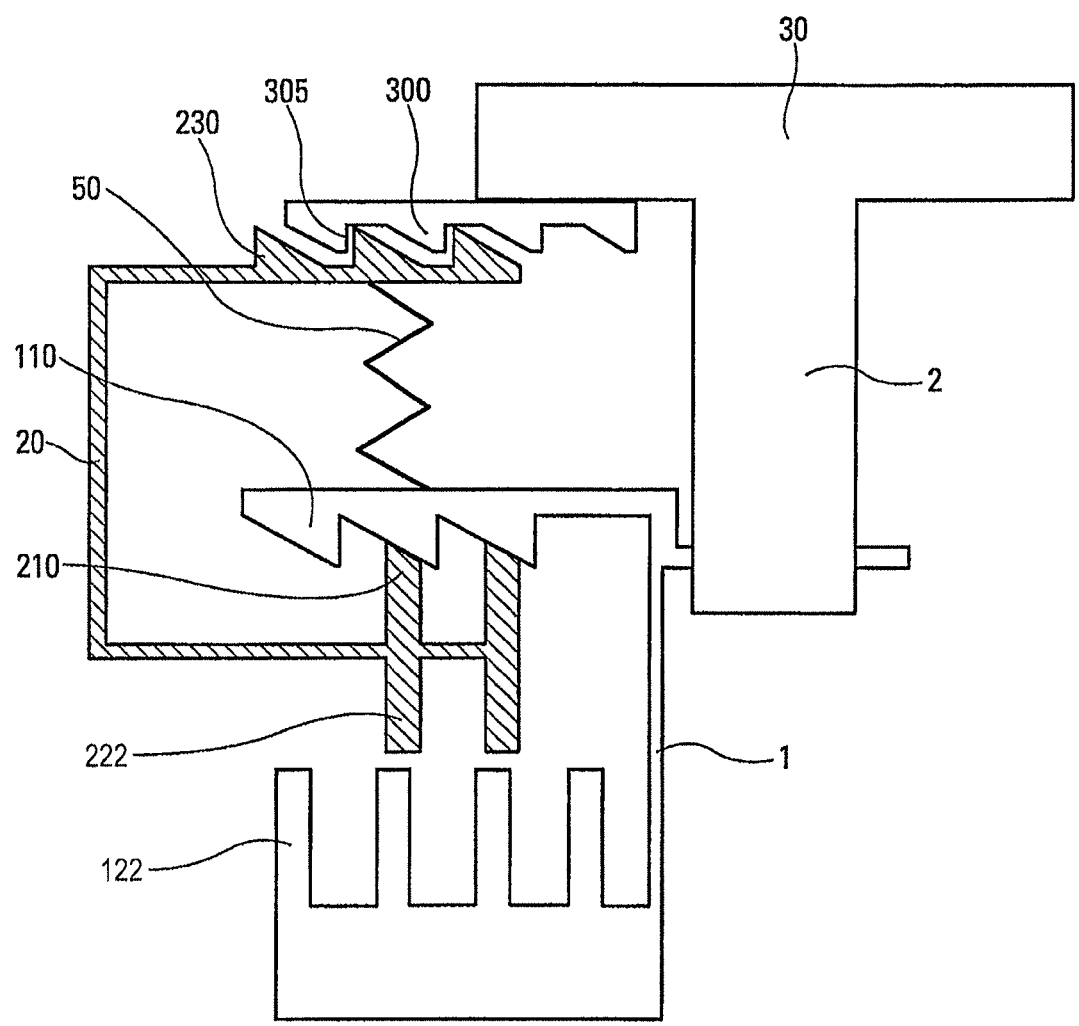
Figure 19:
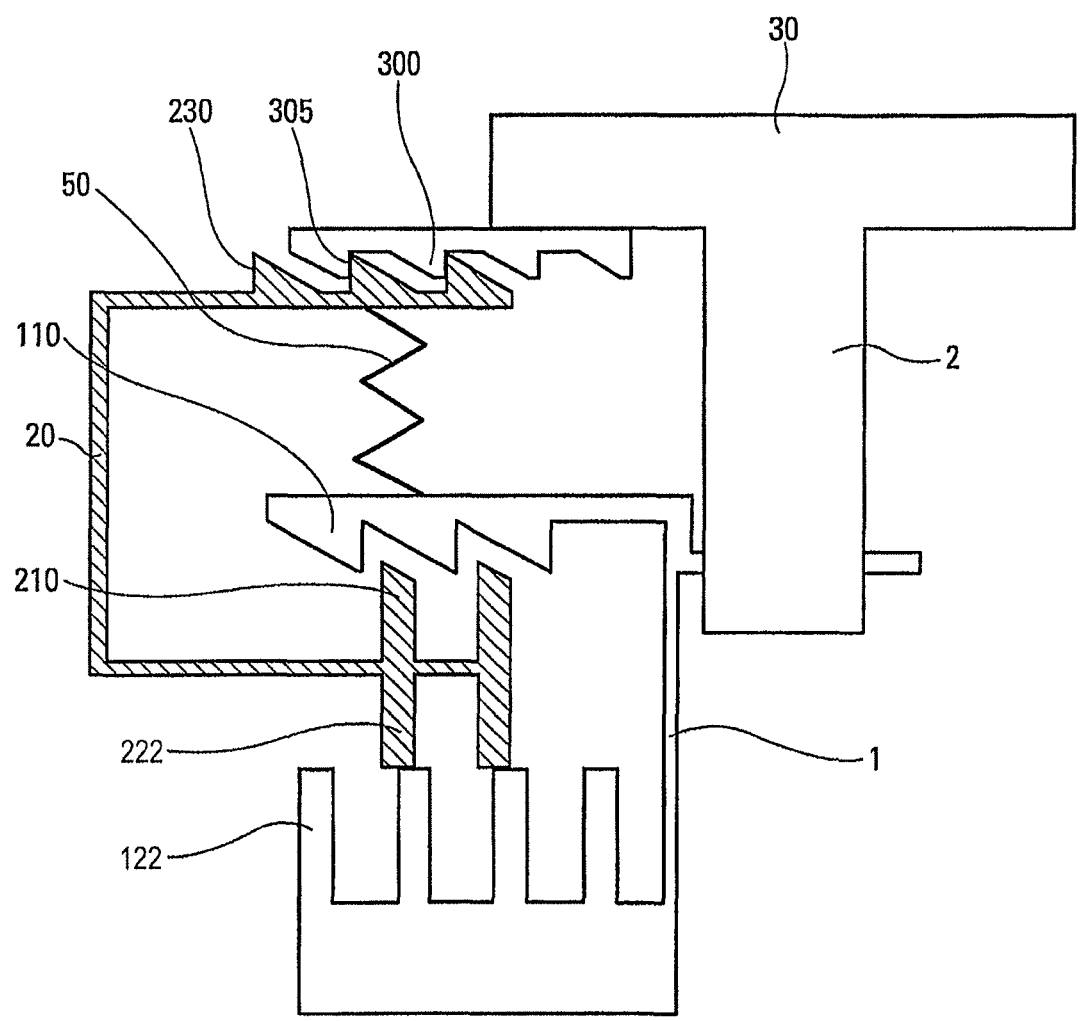
Figure 20:
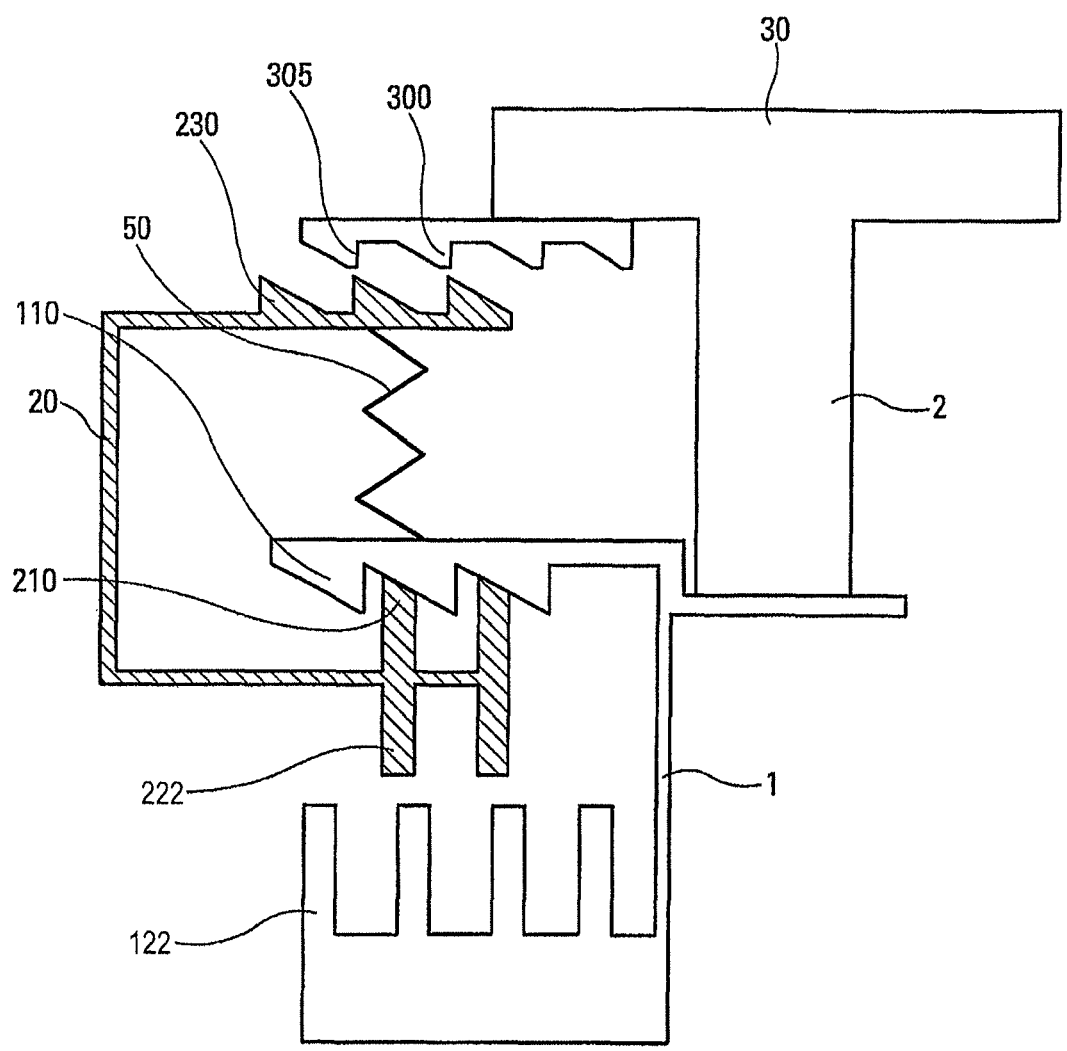

FIG. 16 shows the final actuated position in which the complete actuation stroke has been performed. At this moment, when the user releases the actuation force on the actuator member 30, the system rises under the effect of the return spring 50, and the co-operation between the first gears 210 and 110 of the counter element 20 and the body 1, respectively, causes the counter element to continue to turn. This continued turning is blocked in the actuator gear 300 by abutment means 305. With reference to FIG. 18, if in this position the user presses once again on the actuator member 30, it should be observed that actuation of the dispenser and of the counter device is prevented as a result of the second gear 222 of the counter element, and the second stationary gear 122 of the body 1, facing each other at their plane axial end-profiles. FIG. 19 shows an attempt to perform an actuation while the second safety system is operational. For the dispenser and the dose indicator device to be actuated once again, it is necessary to perform a predetermined incomplete return stroke, which is shown in FIG. 20. If from this position the user actuates again, the counter element 20 would turn, thereby enabling the dispenser and the indicator device to be actuated once again.

Figure 21:
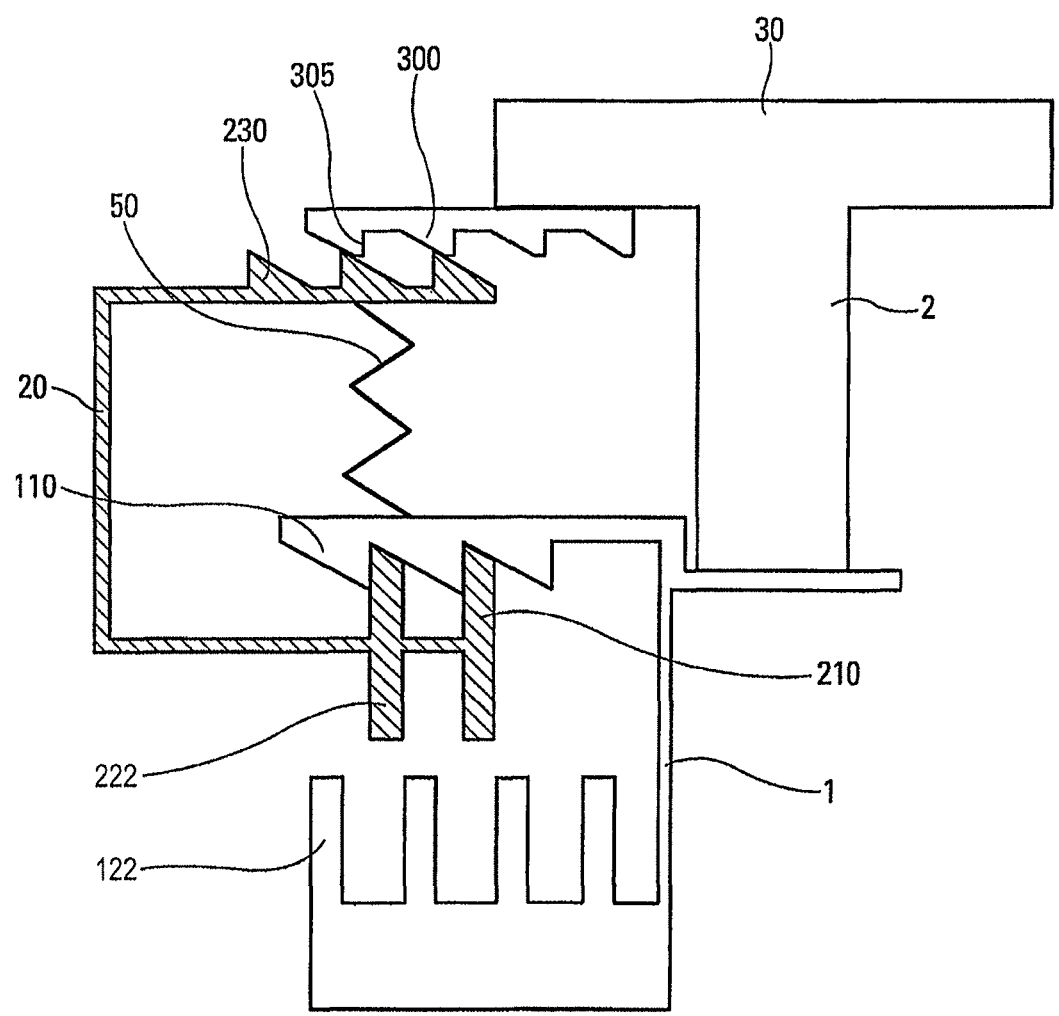

Finally, FIG. 21 shows the position in which such an attempt to perform an additional actuation is made, after said incomplete return stroke has been completed.

Naturally the detailed description of the three embodiments given above is not limiting, and other embodiments can be envisaged without going beyond the ambit of the present invention, as defined by the accompanying claims.

The invention claimed is:

1. A fluid dispenser comprising:
a plurality of displayable dose values;
a stationary body comprising at least one stationary multi-toothed gear;
a first member that is displaceable axially relative to said stationary body;
a second member that is displaceable axially and in rotation relative to said stationary body, said second member being engageable with said first member and said stationary body; and
when said first member displaces axially, the stationary body is configured to allow a fluid reservoir to be axially displaceable relative to said stationary body and said second member is caused to be displaced axially and permitted to rotate relative to said stationary body, so as to change a displayed dose value from among the plurality of displayable dose values,
wherein the stationary body, the first member, and the second member are arranged to have a common central longitudinal axis, and the first member is displaceable axially along the central longitudinal axis, and the second member is displaceable axially aloe the central longitudinal axis and is displaceable rotationally around the central longitudinal axis.

2. The fluid dispenser according to claim 1, wherein the second member comprises at least one multi-toothed gear.

3. A fluid dispenser comprising:
a plurality of displayable dose values;
a stationary body comprising at least one stationary multi-toothed gear;
a fluid reservoir disposed on said stationary body so as to be axially displaceable relative to said stationary body;
a first member that is displaceable axially relative to said stationary body;
a second member that is displaceable axially and in rotation relative to said stationary body, said second member being engageable with said first member and said stationary body; and
when said first member displaces axially, said second member is caused to be displaced axially and permitted to rotate relative to said stationary body, so as to change a displayed dose value from among the plurality of displayable dose values,
wherein the stationary body, the first member, and the second member are arranged to have a common central longitudinal axis, and the first member is displaceable axially along the central longitudinal axis, and the second member is displaceable along the central longitudinal axis and is displaceable rotationally around the central longitudinal axis.

4. The fluid dispenser according to claim 3, wherein the fluid reservoir is configured to be axially displaced relative to said stationary body during actuation of the fluid dispenser.

* * * * *